United States Patent [19]

Anderson et al.

[11] Patent Number: 4,764,633

[45] Date of Patent: Aug. 16, 1988

[54] FERRIC ION CATALYZED COMPLEXATION OF ZINC AND/OR MANGANESE WITH ALPHA AMINO ACIDS

[75] Inventors: Michael D. Anderson; Dean R. Anderson, both of Deephaven, Minn.

[73] Assignee: Zinpro Corporation, Chaska, Minn.

[21] Appl. No.: 91,391

[22] Filed: Aug. 31, 1987

[51] Int. Cl.[4] .......................... C07F 3/06; C07F 13/00
[52] U.S. Cl. ........................................ 556/50; 556/36; 556/134; 548/104
[58] Field of Search ............... 556/50, 134, 36; 548/104

[56] References Cited

U.S. PATENT DOCUMENTS

| | | | |
|---|---|---|---|
| 2,745,859 | 5/1956 | Norton | 556/134 |
| 2,840,587 | 6/1958 | Norton | 556/134 |
| 2,872,469 | 2/1959 | Stevens | 556/50 |
| 3,463,858 | 5/1969 | Anderson | 424/289 |
| 3,916,004 | 10/1975 | Okada | 556/134 |
| 3,925,433 | 12/1975 | Abdel-Monem | 260/438.5 |
| 3,941,818 | 3/1976 | Abdel-Monem | 260/429.9 |
| 3,950,372 | 4/1976 | Abdel-Monem | 260/429 R |
| 4,021,569 | 5/1977 | Abdel-Monem | 424/289 |
| 4,039,681 | 8/1977 | Abdel-Monem | 424/289 |
| 4,067,994 | 1/1978 | Anderson et al. | 424/295 |
| 4,172,072 | 10/1979 | Ashmead | 556/50 |
| 4,216,143 | 8/1980 | Ashmead | 556/50 |
| 4,546,195 | 10/1985 | Helbig | 556/50 |
| 4,618,625 | 10/1986 | Vinas | 556/134 |

*Primary Examiner*—Michael L. Shippen
*Attorney, Agent, or Firm*—Zarley, McKee, Thomte, Voorhees & Sease

[57] ABSTRACT

A method of making 1:1 complex salts of alpha amino acids and a metal ion which is either zinc or manganese, the method comprising reacting a water soluble zinc salt or manganese salt with an alpha amino acid in the presence of catalytically effective amount of ferric ion which aids in solubilizing the metal salt while simultaneously enhancing the formation of 1:1 complexes between the selected zinc or manganese salt and the desired alpha amino acid, particularly methionine.

19 Claims, No Drawings

FERRIC ION CATALYZED COMPLEXATION OF ZINC AND/OR MANGANESE WITH ALPHA AMINO ACIDS

BACKGROUND OF THE DISCLOSURE

This invention relates to an improvement in the process of making 1:1 zinc and 1:1 manganese complexes with alpha amino acids, particularly methionine. In that sense, it represents an improvement over the processes disclosed in commonly owned U.S. Pat. Nos. 3,941,818 issued Mar. 2, 1976, entitled "1:1 ZINC METHIONINE COMPLEXES" and 3,950,372 issued Apr. 13, 1976, and entitled "1:1 MANGANESE ALPHA AMINO ACID COMPLEXES".

Both of the previously issued patents relate to the 1:1 complexed salts per se, and to general processes for preparing the same. The novel salts have as expressed in the earlier issued patents, the useful feature of being highly body absorbable nutritional supplements for both animals and humans to provide readily available sources of zinc ions on the one hand, and manganese ions on the other hand.

In the commercial preparation of these 1:1 metal amino acid complexes, there have been from time to time certain problems in solubilizing the precursor salts and the alpha amino acid, both of which exist in solid powdered form. As a result, even though the salts are theoretically highly soluble in water, the amount of necessary mixing to assure substantial dissolving (even at elevated temperatures) in order to provide the necessary intimate contact for adequate reacting between the two to form 1:1 complexes of the zinc and/or manganese and the alpha amino acid is quite excessive. Thus, there has been an inherent problem in the preparation technique, both from the standpoint of the very practical problem of adequate dissolving even in hot water, and also the problem of assuring that the product is substantially all the desired 1:1 complexes.

Accordingly, there has been a real and a continuing need for the discovery of process improvements which allows the ready dissolving of the initial precursor reactants or ingredients, and which will simultaneously assure product yield in high amounts of the desired 1:1 complexes of the metal ions and the alpha amino salts.

This invention has as its primary objective the fulfillment of this need in order that the 1:1 manganese alpha amino acid complexes of U.S. Pat. No. 3,950,372 and the 1:1 zinc alpha amino acid complexes of U.S. Pat. No. 3,941,818, may be prepared easily without long process delays and in high yield of the desired 1:1 complexes.

For details of desirability and utility of 1:1 manganese alpha amino acid complexes, see the previously referred to U.S. Pat. No. 3,950,372 which is incorporated herein by reference. For details of desirability and utility of 1:1 zinc alpha amino acid complexes, see U.S. Pat. No. 3,941,818 which is incorporated herein by reference.

The method of accomplishing each of the objectives of this invention will become apparent from the detailed decription of the invention which follows hereinafter.

SUMMARY OF THE INVENTION

This invention relates to a process improvement which allows increased ease of preparation in high yields of 1:1 complexes of zinc and manganese with alpha amino acids to provide in high yield the desired 1:1 complexes in a form which can be readily absorbed biochemically after ingestion by animals and humans to provide adequate and proper dietary levels of zinc and methionine as necessary for proper health, weight gain and dietary balance. The reaction is a straightforward reaction between the respective zinc salt and the respective manganese salt and the alpha amino acid, which are both at least partially dissolved in water. It is significantly catalyzed, both from the standpoint of solubilization of the respective salts and from the standpoint of producing the desired 1:1 complexes between the respective zinc ion and manganese ion and the desired alpha amino acid, preferably methionine, by conducting the reaction in the presence of catalytically effective amount of ferric ion, preferably in the form of ferric sulfate.

DETAILED DESCRIPTION OF THE INVENTION

It is important to note that the respective zinc and manganese compounds which are prepared in accordance with this invention are referred to as complexed salts. These salts are to be carefully distinguished from conventional salts such as, for example, zinc chloride or manganese chloride. Such conventional salts such as zinc chloride or manganese chloride contain only an electrostatic attraction between the cation and the anion. The 1:1 complexed salts prepared by this invention differ from conventional salts in that while they have an electrostatic attraction between the cation and the anion, there is also a coordination bond between the cation and the amino moiety of the alpha amino acid.

The preferred alpha amino acid for use in this invention is methionine. From the standpoint of both zinc complex salts and the manganese complex salts, however, it should be understood that other alpha amino acids may be employed as well. Preferably those are essential alpha amino acids. Those essential alpha amino acids which are preferred for utilization in forming the 1:1 complex salts of this invention are arginine, histidine, isoleucine, leucine, lysine, methionine, phenylalanine, threonine, tryptophane, and valine. Glycine, while not an essential amino acid, is also a preferred alpha amino acid in that it is readily available and can be utilized for synthesis of the complex salts of this invention. The two most preferred natural alpha amino acids are methionine and glycine.

With regard to the preferred zinc methionine complexed salts which are prepared in accordance with the improved process of this invention, they have the general formula:

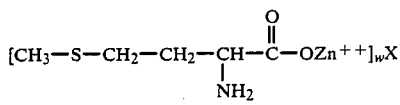

wherein X is an anion and w is an integer equal to the anionic charge of X. The cation of these complexed salts is represented by the bracketed material in the above formula and represents a 1:1 complex of zinc and methionine.

With regard to the manganese alpha amino acid complex salts of the present invention, they have the formula:

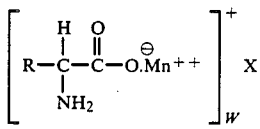

wherein R is an alpha moiety of alpha amino acid, preferably methionine or glycine, X is an anion, and W is an integer equal to the anion charge of X. The cation of these complexed salts is represented by the bracketed material in the above formula and represents a 1:1 complex of manganese and alpha amino acid.

The process of preparing the desired zinc and methionine 1:1 complex salts of the alpha amino acids referred to herein, in each instance as the earlier patents mention, is straightforward and direct. Commonly it begins with the use of a water soluble zinc salt and/or a water soluble manganese salt, respectively. Suitable zinc salts which can be employed are the halides, the sulfates, and the phosphates. The desired weight ratio of zinc salt to methionine is within the range of 1:1 to 2:1, preferably 3:2. Suitable manganese salts which can be employed are likewise halides, sulfates and phosphates. The desired weight ratio of manganese to methionine is 1:1 to 2:1, preferably 4:3. In each instance, the sulfate salts are preferred from the standpoint of availability and, at least currently, cost.

In the general process, these salts are at least partially water dissolved, preferably at elevated temperatures. Temperatures within the range of from about 180° F. to about 205° F. have been found desirable, most preferably temperatures with the range of 190° F. to about 205° F. In actual practice, one common technique is to stir the salt into a water solution while simultaneously injecting steam to elevate the temperature within the desired range.

In the most preferred embodiment of the present invention the catalytic ferric ion is next added. It should be understood, however, that the catalytic amount of ferric ion can be added both before the addition of the alpha amino acid or after, with before being modestly preferred.

As previously mentioned, it has been discovered that when the reaction between the water soluble metal salt and the alpha amino acid is conducted in the presence of a catalytically effective amount of ferric ion, two desirable things occur. In the first instance, the dissolving of the salt and the amino acid in the water appears to be significantly enhanced from the standpoint of rapidity and in the second instance, there is an increased yield of the desirable 1:1 complexes formed.

It is not known precisely why the ferric ion catalyzes the process, but it nevertheless does. The ferric ion may be added in the form of any water soluble salt such as ferric chloride, ferric sulfate, ferric phosphate, ferric acetate or any other suitable water soluble ferric salt. The most preferred are ferric chloride and ferric sulfate. The amount added can be from about 2% to about 10% based upon the dry weight of alpha amino acid, preferably from about 4% to about 8% based upon the dry weight of alpha amino acid employed. For the most preferred alpha amino acid of this invention, methionine, 4% by weight has been found best in experimentation to date. However, it should be understood that any amount within the range from about 2% up to about 10% by weight of the alpha amino acid will work. The lower limit expressed herein, i.e., 2%, is about the minimum quantity needed for any significant improvement. The upper level is a practical and economic level, since amounts in excess do not seem to add anything except expense. After the preferred catalytic amount of ferric ion is added to the water soluble salt of either zinc or manganese, and mixed therein, the desired alpha amino acid is then stirred into the reaction mixture along with increased injection of steam in order to elevate the temperature again to within the desired temperature range.

It is noted in the reaction process that where the ferric ion is used, almost immediately the solution becomes clear, lumping does not occur, and in the case of zinc methionine complexes, it immediately turns to a clear reddish brown solution. In the case of manganese methionine complexes, the reaction immediately turns to a distinct clear solution of similar color. In both instances, there is no problem of "lumping" and the reaction becomes straightforward and direct to the desired 1:1 complexes.

After the reaction is completed, which is ordinarily a matter of minutes, but may be up to an hour or longer if desired, the product is ready for finishing.

If product concentrate is desired, it may be spray dried in each instance. On the other hand, if the product is to be mixed with a carrier, such as a cereal product, it may be mixed together at varying ratios, put into drying drums, and dry coated on the cereal product.

The following examples are offered to further illustrate the improved process of this invention.

EXAMPLE 1

(Preparation of 1:1 Zinc Methionine Complexes)

This process prepares in batch form a 1,010 pound batch of product.

Five hundred pounds of water are heated to within the range of from 200° F. to 205° F. by injecting steam into a batch holding stainless steel vessel. Three hundred pounds of reagent grade zinc sulfate are added to the vessel, while continually stirring the same. Simultaneously 10 pounds of ferric sulfate are added and steam is continuously injected in order to maintain the temperature within the range of 200° F. to 205° F. Thereafter, 200 pounds of methionine is added, while continuously stirring.

Immediately, the reaction product turns clear, all lumping is elminated, and the product appears to be a true solution, reddish brown in color. When it is readily apparent that everything is dissolved and nothing is in suspension, the product is then passed to a spray dryer and spray dried to provide a 1:1 zinc methionine complex.

The formation of the 1:1 complex is confirmed by infrared analysis, titration curve analysis, and quantitative analysis. Such was found to be present in excess of a 90% yield of the desired product.

EXAMPLE 2

(Formation of 1:1 Manganese Alpha Amino Acid Complexes)

A substantially similar process as used in Example 1 is done with the following changes. In this instance again the amount of the batch was 1,010 pounds, 500 pounds of water, and 500 pounds of solids. In the solids, the manganese salt employed was manganese sulfate, and the ferric catalyst employed was again ferric sulfate. The amount of manganese sulfate employed was 286 pounds, and the amount of methionine employed was 214 pounds. The ratio of these was 4:3. The amount of catalyst employed was 10 pounds.

Again, it was evident that no lumping occurred, that there was a true solution formed, and that the reaction was nearly instantaneously complete upon stirring with the reactants present. Again, the desired 1:1 manganese methionine complex was formed in a yield in excess of 90%.

It therefore can be seen that the invention accomplishes at least all of its stated objectives.

What is claimed is:

1. A method of making a 1:1 complex salt of an alpha amino acid and a metal ion selected from the group consisting of zinc and manganese, said method comprising:

reacting a water soluble metal salt selected from the group consisting of zinc salts and manganese salts which are at least partially water dissolved, with an alpha amino acid selected from the group consisting of arginine, histidine, isoleucine, leucine, lysine, methionine, phenylalanine, theronine, tryptophane, valine and glycine, said reaction occurring in the presence of a 1:1 complexing catalytically effective amount of ferric ion.

2. The method of claim 1 wherein the alpha amino acid is methionine.

3. The method of claim 2 wherein the metal salt is a zinc salt.

4. The method of claim 3 wherein the zinc salt is zinc sulfate.

5. The method of claim 2 wherein the metal salt is a manganese salt.

6. The method of claim 5 wherein the manganese salt is manganese sulfate.

7. The method of claim 3 wherein the sourc of ferric ion is ferric sulfate.

8. The method of claim 6 wherein the source of ferric ion is ferric sulfate.

9. The method of claim 1 wherein at least the partially dissolved salt solution of a metal ion selected from the group consisting of zinc salts and manganese salts is initially heated to a temperature of from 180° F. to about 205° F. group.

10. The method of claim 9 wherein the initial heating is to a temperature of from 190° F. to about 205° F.

11. The method of claim 9 wherein the reactants are continually mixed during the addition of said alpha amino acid.

12. The method of claim 4 wherein the weight ratio of zinc sulfate to methionine is within the range of from 1:1 to 2:1.

13. The method of claim 12 wherein the weight ratio of zinc sulfate to methionine is about 3:2.

14. The method of claim 6 wherein the weight ratio of manganese sulfate to methonine is within the range of from 1:1 to 2:1.

15. The method of claim 14 wherein the weight ratio of manganese sulfate to methionine is about 4:3.

16. A method of making a 1:1 complex of zinc and methionine, said method comprising:

reacting a water soluble zinc salt which is at least partially water dissolved with methionine, said reaction occurring in the presence of a 1:1 complexing catalytically effective amount of ferric ion.

17. The process of claim 16 wherein said ferric ion is provided by ferric sulfate.

18. A method of making a 1:1 complex of an alpha amino acid and manganese, said method comprising:

reacting a water soluble manganese salt with an alpha amino acid selected from the group consisting of arginine, histidine, isoleucine, leucine, lysine, methione, phenylalanine, theronine, tryptophane, valine and glycine, said reaction occurring in the presence of a 1:1 complexing catalytically effective amount of ferric ion.

19. The reaction of claim 19 wherein said manganese salt is manganese sulfate.

* * * * *